(12) United States Patent
Standish (10) Patent No.: US 7,021,932 B2
(45) Date of Patent: Apr. 4, 2006

(54) TOOTH EXTRACTION DEVICE

(76) Inventor: Edward B. Standish, 8904, 150th Ave. KPN, Gig Harbor, WA (US) 98329

( * ) Notice: Subject to any disclaimer, the term of this patent is extended or adjusted under 35 U.S.C. 154(b) by 326 days.

(21) Appl. No.: 10/615,562

(22) Filed: Jul. 8, 2003

(65) Prior Publication Data

US 2005/0008987 A1    Jan. 13, 2005

(51) Int. Cl.
  *A61C 3/00*    (2006.01)
  *A61B 17/28*   (2006.01)
(52) U.S. Cl. .................. 433/157; 433/159; 606/205
(58) Field of Classification Search .............. 433/1, 433/4, 157, 159, 160; 606/205; 294/19.1, 294/24, 106, 111
See application file for complete search history.

(56) References Cited

U.S. PATENT DOCUMENTS

| 1,147,580 | A |   | 7/1915 | Turner |
|---|---|---|---|---|
| 2,027,470 | A | * | 1/1936 | Caruso ................. 433/158 |
| 2,210,349 | A |   | 8/1940 | Beeck |
| 2,430,271 | A |   | 11/1947 | Brantley |
| 4,230,454 | A |   | 10/1980 | Lococo |
| 4,443,196 | A |   | 4/1984 | Rico |
| 4,669,769 | A | * | 6/1987 | Polder, Jr. .................. 294/19.1 |
| 4,669,979 | A | * | 6/1987 | Snead ............................ 433/4 |
| 5,105,185 | A |   | 4/1992 | Nakanowatari et al. |
| 5,209,747 | A | * | 5/1993 | Knoepfler .................... 606/16 |
| 5,306,141 | A |   | 4/1994 | Sears |
| 5,478,350 | A | * | 12/1995 | Kratsch et al. ............. 606/205 |
| 5,620,459 | A | * | 4/1997 | Lichtman .................... 606/205 |
| 5,766,205 | A | * | 6/1998 | Zvenyatsky et al. ........ 606/206 |
| 5,904,482 | A |   | 5/1999 | Long et al. |

* cited by examiner

*Primary Examiner*—Ralph A. Lewis
(74) *Attorney, Agent, or Firm*—Dale J. Ream (57) ABSTRACT

A tooth extraction device is provided that uses a clamp assembly to clamp a tooth to be extracted, and a handle for positioning the clamp assembly within a patient's mouth. A cable and an actuator for moving the cable are provided for moving the clamp assembly. The clamp assembly includes a pair of clamp links pivotally connected to a carrier block. The carrier block is slidably movable relative to the handle to extract the tooth after the clamp links are rotated into engagement with opposite sides of the tooth. A base tooth support engages a first neighboring tooth on a proximal side of the clamp assembly, and a removable tooth support engages a second neighboring tooth on a distal side of the clamp assembly. The tooth supports distribute the force of extracting a tooth over the neighboring teeth, thereby allowing more control in manipulating the device during a tooth extraction.

13 Claims, 7 Drawing Sheets

TOOTH EXTRACTION DEVICE

BACKGROUND OF THE INVENTION

1. Field of the Invention

The present invention relates generally to dental devices, and in particular, to dental devices used for extracting teeth.

2. Description of the Related Art

A number of prior art devices exist for the purpose of extracting a tooth or removing a dental prosthesis, crowns and the like. The use of such devices to extract teeth is often associated with pain and unpleasantness. Part of the pain originates from the simple tools that dentists currently use to extract teeth. Specifically, the forceps and elevators that are currently used by dentists require brute force to be applied by the dentist in removing the tooth. This results in unnecessary pain and discomfort, as the tooth must be worked out, and often the use of such tools results in damage to the socket of the extracted tooth.

Attempts have been made to overcome the drawback of using forceps and elevators. For example, a tooth extractor system is disclosed in U.S. Pat. No. 4,230,454 issued to Lococo, which utilizes a tooth engaging grip means selectively connectable to a lever which, in turn, is rested against a base normally located on a tooth or teeth adjacent the tooth root to be extracted. This prior art tooth extractor system had the advantage of requiring less physical power from the dentist, thus enabling a more accurate operation with reduced damage of the socket of the extracted tooth.

However, the tooth extractor system described in the '454 patent suffered from a relatively complex assembly of parts that would have limited its usefulness. The attachment of the tooth engaging grip means to a tooth to be extracted and the placement of the separate base component on the adjacent tooth would have required substantial skill on the part of the dentist to position the tools and complete the procedure. For at least these reasons and perhaps others, the tooth extractor system described in the '454 patent apparently did not become widely established on the market.

Various other dental forceps or so-called "fulcrum forceps" also exist in the prior art, which have found only limited success in the market. For example, U.S. Pat. No. 1,147,580 issued to Turner, U.S. Pat. No. 2,430,271 issued to Brantley, and U.S. Pat. No. 4,443,196 issued to Rico all disclose tooth extractor devices that use a fulcrum in conjunction with either a tooth clamp or a tooth root screw to facilitate removing a tooth or a tooth root from a patient. However, none of these devices provide an acceptable tool for simplifying the tooth extraction procedure and minimizing pain and unpleasantness as a tooth is worked out.

There is a need in the industry for an improved tooth extraction device to overcome these and other problems associated with the prior art.

SUMMARY OF THE INVENTION

An object of the present invention is to provide an improved tooth extraction device that overcomes the problems and shortcomings of the prior art.

A further object of the present invention is to provide a tooth extraction device that incorporates many unique and improved features to make tooth extraction as pleasant as possible.

A further object of the present invention is to provide a tooth extraction device that automatically clamps onto a tooth before pulling up on the tooth.

A further object of the present invention is to provide a tooth extraction device that can be adapted easily to perform a wide range of extractions and other different functions.

A further object of the present invention is to provide an improved tooth extraction device that can be operated in the narrow confines of a patient's mouth, that can precisely control the location and force applied to the tooth, and that provides an initial clamping force to securely grip the tooth followed by a pull force that removes the tooth.

A further object of the present invention is to provide an improved tooth extraction device that is economical to manufacture, easy to use, and capable of a long operating life.

In order to accomplish these and other objects of the invention, a tooth extraction device is provided that uses a clamp assembly to clamp a tooth to be extracted, and a handle for positioning the clamp assembly within a patient's mouth. A cable and an actuator for moving the cable are provided for moving the clamp assembly. The clamp assembly includes a pair of clamp links pivotally connected to a carrier block. The carrier block is slidably movable relative to the handle to extract the tooth after the clamp links are rotated into clamping engagement with opposite sides of the tooth. Movement of the cable causes the clamp links to first rotate into engagement with opposite sides of a tooth and then causes the carrier block to slide along the handle to extract the tooth.

A base tooth support engages a first neighboring tooth on a proximal side of the clamp assembly, and a removable tooth support engages a second neighboring tooth on a distal side of the clamp assembly. The tooth supports distribute the force of extracting a tooth over the neighboring teeth, thereby allowing more control by the dentist in manipulating the device during a tooth extraction.

According to another broad aspect of the present invention, a tooth extraction device is provided, comprising: a handle; a clamp assembly attached to the handle, the clamp assembly comprising a structure for clamping a tooth to be extracted; and a cable attached to the clamp assembly for moving the clamp assembly relative to the handle to extract a tooth.

According to another broad aspect of the present invention, a tooth extraction device is provided, comprising: a handle; a clamp means attached to the handle for clamping a tooth to be extracted; and a drive means for sequentially pivoting the clamp means into engagement with the tooth to be extracted and then sliding the clamp means relative to the handle to extract the tooth.

Numerous other objects of the present invention will be apparent to those skilled in this art from the following description wherein there is shown and described a preferred embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE PREFERRED EMBODIMENT

Figure 1:
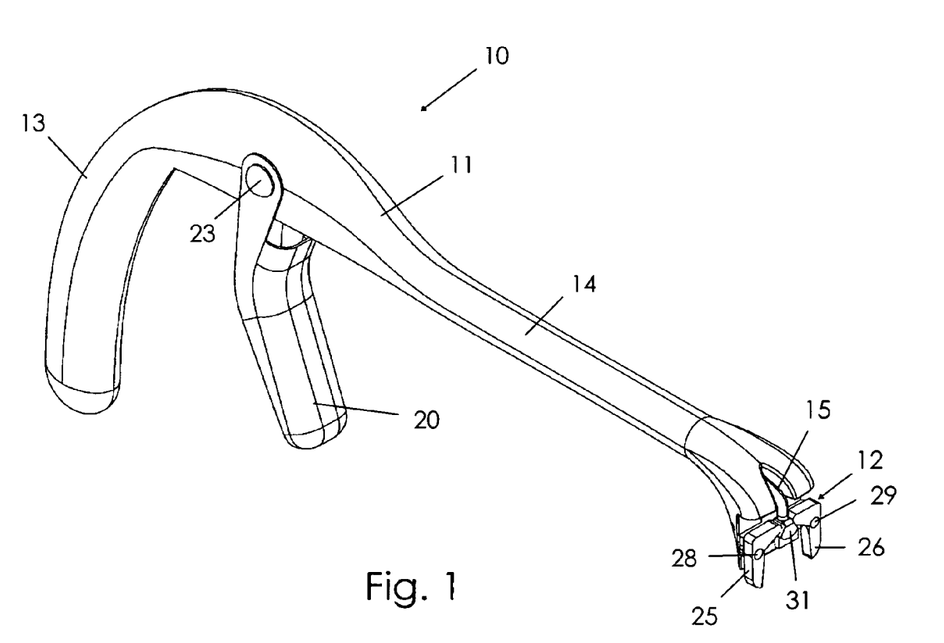
FIG. 1 is a perspective view of a tooth extraction tool according to a first embodiment of the present invention.
Figure 2:
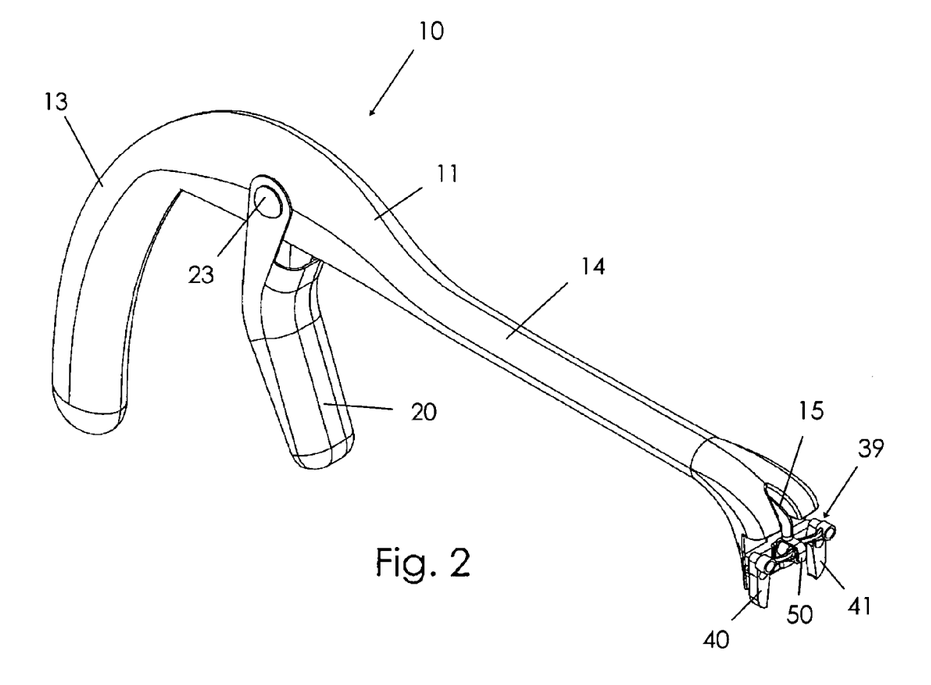
FIG. 2 is a perspective view of a tooth extraction tool according to a second embodiment of the present invention.
Figure 3:
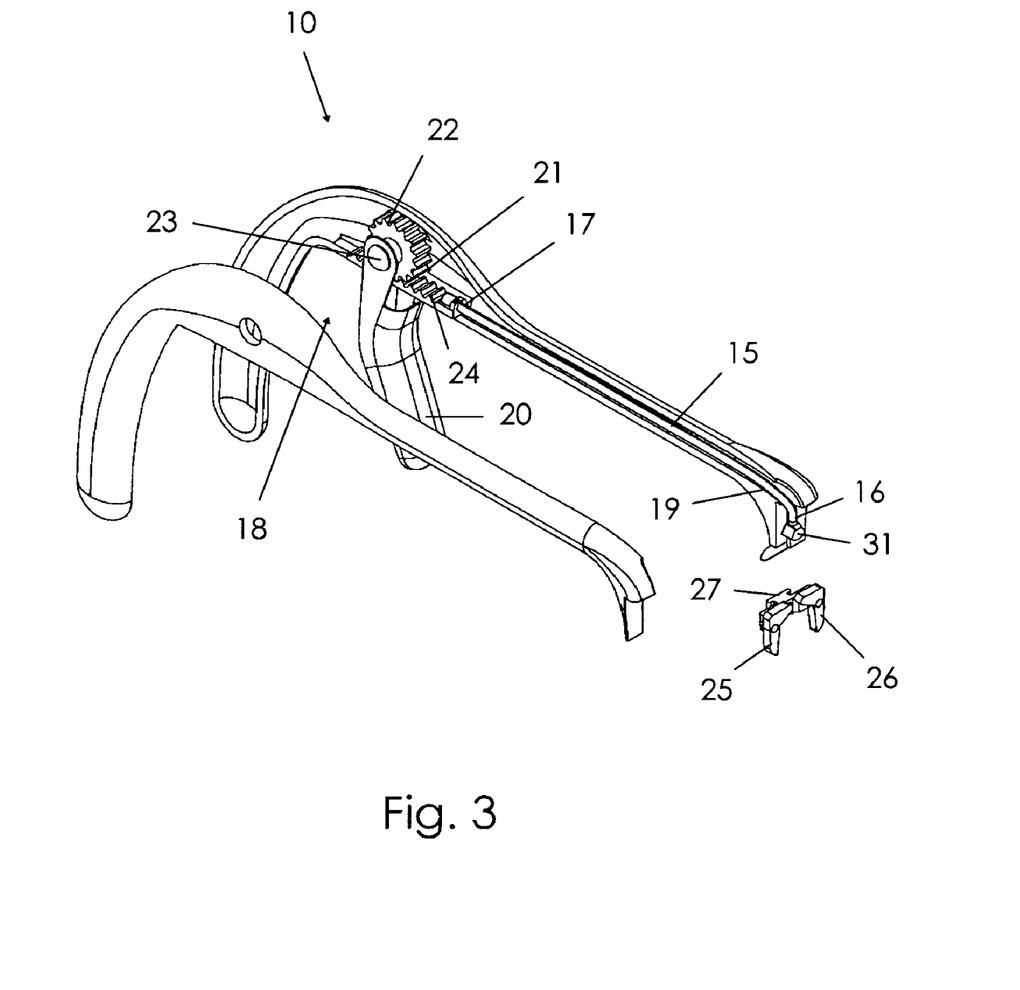
FIG. 3 is an exploded perspective view showing the internal components of the tooth extraction tool of the first embodiment shown in FIG. 1.
Figure 4A:
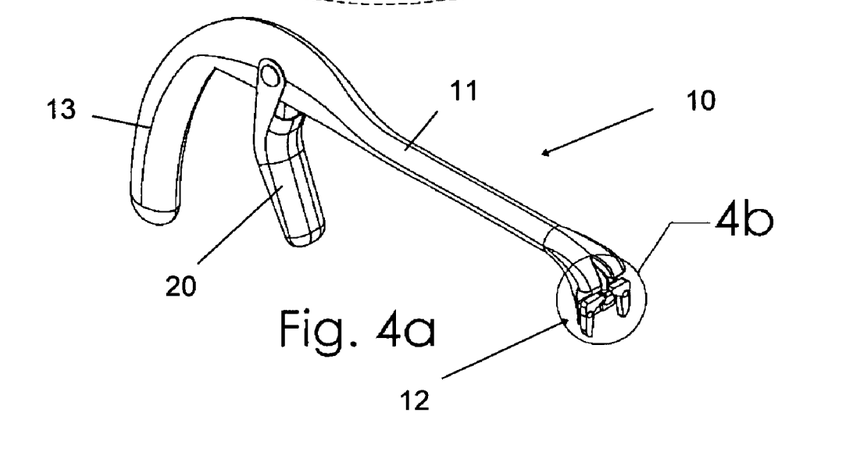
FIGS. 4a and 4b are perspective and enlarged detail perspective views, respectively, of a clamp assembly portion of the tooth extraction tool according to the first embodiment of the present invention.
Figure 4B:
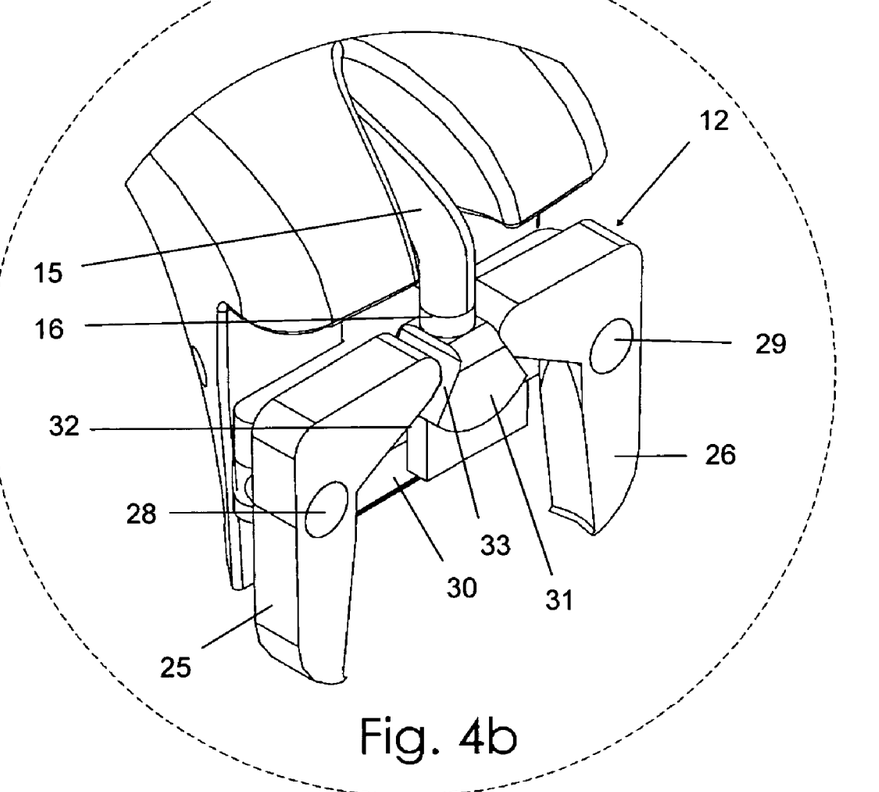
Figure 5A:
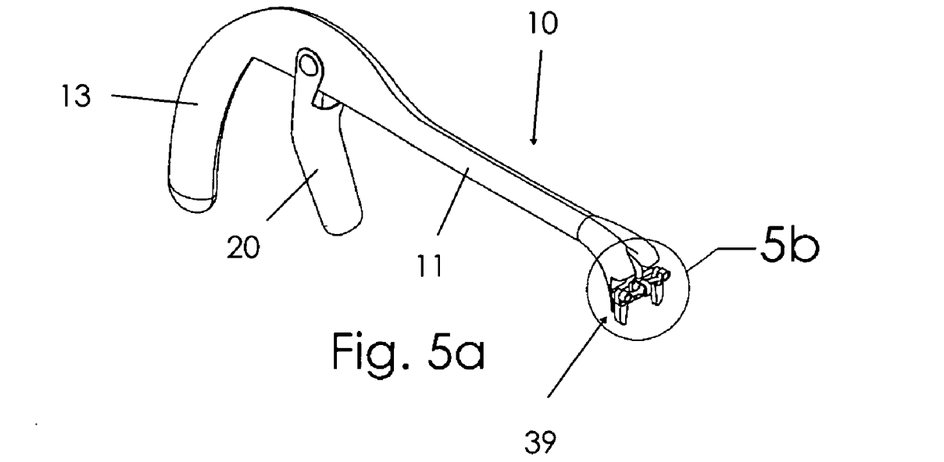
FIGS. 5a and 5b are perspective and enlarged detail perspective views, respectively, of a clamp assembly portion of the tooth extraction tool according to the second embodiment of the present invention.
Figure 5B:
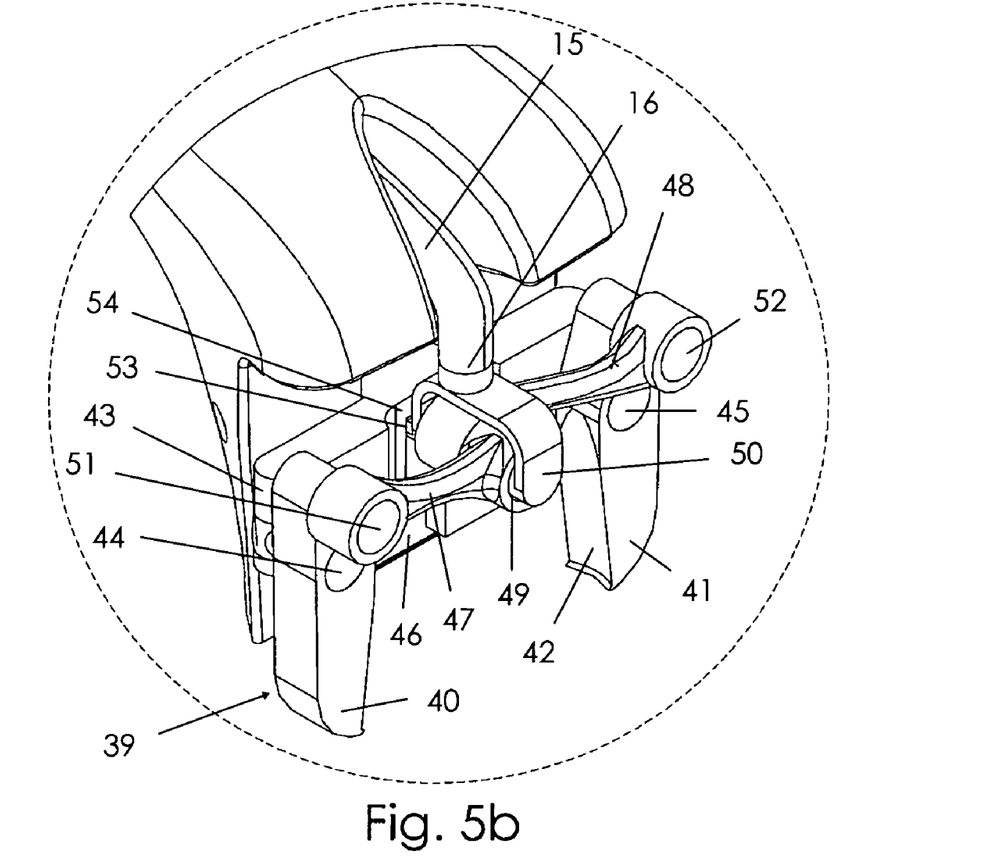
Figures 6A, 6B:
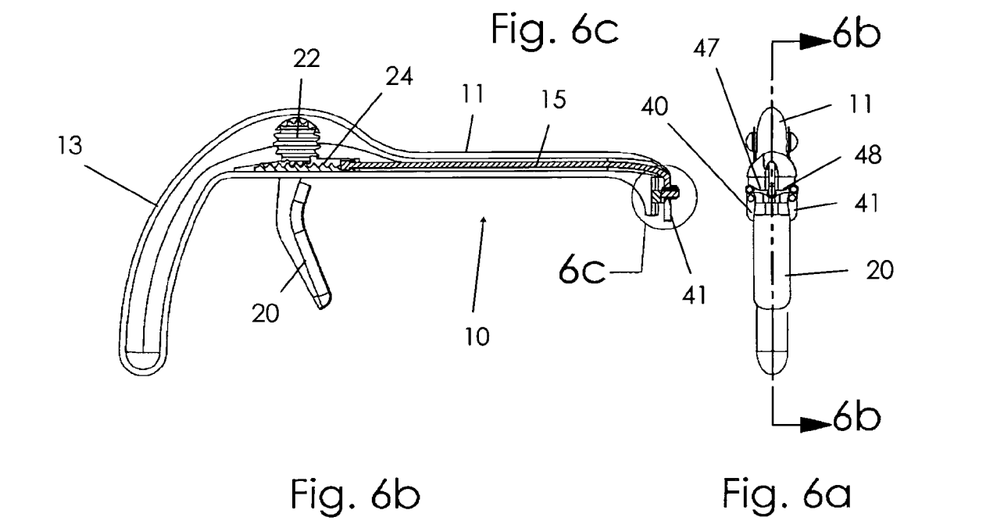
FIGS. 6a, 6b and 6c are an end view, a cross section side view, and an enlarged cross section detail side view, respectively, showing further details of the clamp assembly portion of the tooth extraction tool of the second embodiment.
Figure 6C:
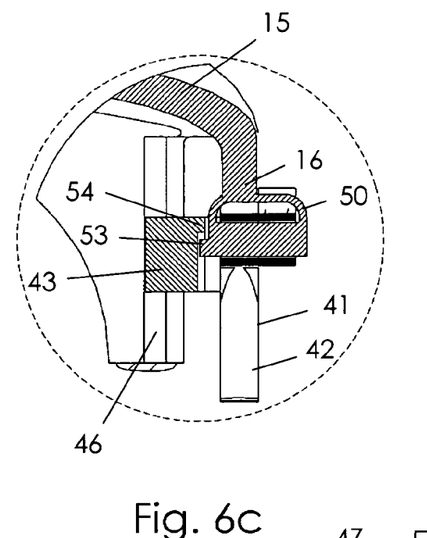
Figure 7A:
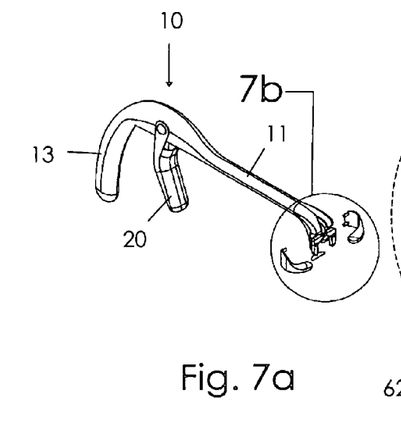
FIGS. 7a, 7b, 7c and 7d are a top perspective view, an enlarged detail top perspective view, a bottom perspective view, and an enlarged detail bottom perspective view, respectively, showing details of support structures for engaging neighboring teeth during a tooth extraction.
Figure 7B:
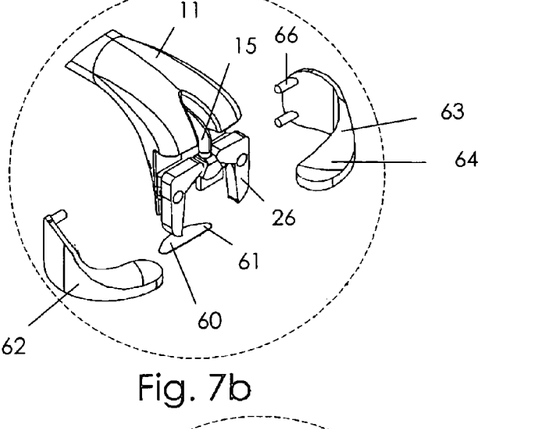
Figure 7C:
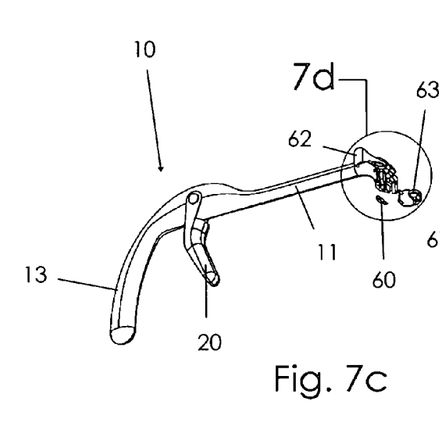
Figure 7D:
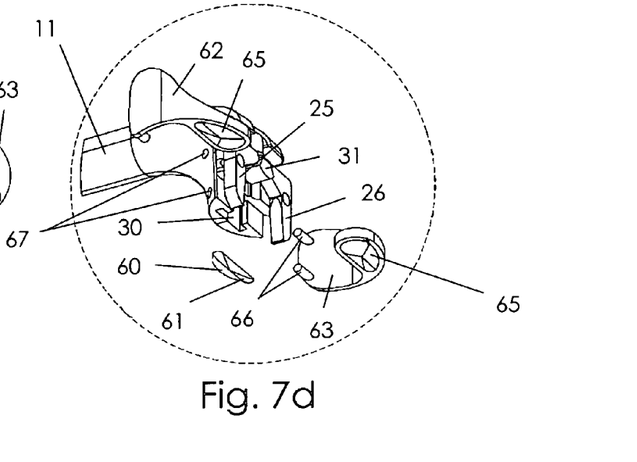

A tooth extraction device according to preferred embodiments of the present invention will now be described with reference to FIGS. 1 to 7d of the accompanying drawings.

The tooth extraction device 10 of the present invention includes a handle 11 and a clamp assembly 12 attached to the handle 11. The handle 11 has a handgrip portion 13 at a first end, the clamp assembly 12 attached to a second end, and an elongated neck portion 14 extending between the first and second ends.

A cable 15 for transmitting power from the handle 11 to the clamp assembly 12 has a first end 16 attached to the clamp assembly 12 and a second end 17 attached to an actuator 18 within the handle 11. The cable 15 extends through the elongated neck portion 14 of the handle 11 and slides along a groove 19 in the housing of the handle 11 to minimize overall height of the handle 11, and particularly the portion to be inserted into a patient's mouth. In the preferred embodiments, the actuator 18 comprises a manually operated trigger 20 with an associated rack and pinion gear assembly 21. The gear assembly 21 includes a pinion 22 connected to the trigger 20 that rotates with the trigger 20 about a pivot axis 23, and a rack 24 connected to the second end 17 of the cable 15. The rack 24 and pinion 22 are intermeshed such that rotation of the trigger 20 causes linear movement of the rack 24 and the cable 15 within the handle 11.

The clamp assembly 12 has a structure for clamping a tooth to be extracted. A key feature of the clamp assembly 12 is that it provides a mechanism that automatically locks onto the tooth before pulling on the tooth. In the first embodiment shown in FIGS. 1, 3, 4a and 4b, the structure for clamping a tooth comprises a pair of clamp links 25, 26 that engage opposite sides of the tooth. The clamp links 25, 26 are pivotally connected to a carrier block 27 at link pivots 28, 29, and are rotatable on the carrier block 27 to engage the opposite sides of the tooth.

The carrier block 27 is slidably mounted in a T-slot 30 or similar guiding structure at the second end of the handle 11. A wedge 31 is attached to the first end 16 of the cable 15. The wedge 31 has a lateral profile or thickness that increases in a direction away from the cable 15. The clamp links 25, 26 each have a corresponding surface 32 that engages a respective opposing side 33 of the wedge 31. The arrangement of the wedge 31 and the corresponding surfaces 32 of the clamp links 25, 26 is such that movement of the wedge 31 relative to the clamp links 25, 26 causes the clamp links 25, 26 to rotate on the carrier block 27. Specifically, as the cable 15 is pulled toward the trigger 20, the widening profile of the wedge 31 is pulled into sliding engagement with the clamp links 25, 26 and causes the clamp links 25, 26 to rotate on the carrier block 27 into locking engagement with the tooth to be extracted. Once the clamp links 25, 26 are in locking engagement with the tooth, further movement of the cable 15 causes the wedge 31 to maintain a locking force on the clamp links 25, 26 while also causing the carrier block 27 to slide along the handle 11 to extract the tooth.

In the tool extraction device 10' according to the second embodiment shown in FIGS. 2 and 5a to 6c, the clamp assembly 39 comprises a pair of clamp links 40, 41 that engage opposite sides of the tooth. The clamp links 40, 41 have inner surfaces 42 for gripping the tooth to be extracted, similar to the clamp links 25, 26 in the first embodiment. The clamp links 40, 41 in the second embodiment are also pivotally connected to a carrier block 43, and are rotatable on the carrier block 43 about link pivots 44, 45 to engage the opposite sides of the tooth to be extracted. The carrier block 43 is mounted for sliding movement in a T-shaped slot 46 or other suitable guiding structure at the second end of the handle 11 and has generally the same structure as the carrier block 27 in the first embodiment.

A pair of toggle links 47, 48 are pivotally connected at a cable pivot 49 to the first end 16 of the cable 15 via a straddle hanger 50 or the like. The toggle links 47, 48 extend laterally in opposite directions from the straddle hanger 50 and are pivotally connected at toggle pivots 51, 52 to the clamp links 40, 41. A stop 53 is provided on the straddle hanger 50 to engage a corresponding structure 54 on the carrier block 43 once the straddle hanger 50 is moved into a toggle position, as explained below. The toggle links 47, 48 are arranged such that movement of the toggle links 47, 48 relative to the carrier block 43 causes the clamp links 40, 41 to rotate on the carrier block 43. Specifically, as the cable 15 is pulled toward the trigger 20, the inner ends of the toggle links 47, 48 are pulled by the straddle hanger 50 and cause the clamp links 40, 41 to rotate on the carrier block 43 into locking engagement with the tooth to be extracted. Once the clamp links 40, 41 are in locking engagement with the tooth, further movement of the cable 15 causes the toggle links 47, 48 to maintain a locking force on the clamp links 40, 41 while also causing the carrier block 43 to slide along the T-shaped slot 46 in the handle 11 to extract the tooth.

The toggle position of the toggle links 47, 48 allows a relatively small input force to be magnified into a high clamping force. When the toggle pivots 51, 52 and the cable pivot 49 are aligned, the linkage is in the toggle position. At this point, no amount of force on the tips of the clamp links 47, 48 will be able to back drive the linkage, and the maximum force will be exerted on the tooth. In operation, the cable 15 raises the toggle links 47, 48 causing the clamp links 40, 41 to pivot about the link pivots 44, 45 and close around the tooth. This continues until the toggle links 47, 48 are in the toggle position. Once this high clamping force position has been achieved, the straddle hanger stop 53 engages the corresponding structure 54 of the carrier block 43 and causes the whole assembly to slide along the T-shaped slot 46 of the handle 11 and extract the tooth.

In both the first and second embodiments described above, the tooth extraction device is preferably equipped with a base support 60 attached to the second end of the handle 11 near the clamp assembly 12, 39. As shown in FIGS. 7*a* to 7*d*, the base support 60 engages one or more neighboring teeth on a proximal side of the tooth to be extracted and provides a reaction force to facilitate extracting the tooth. The base support 60 preferably includes a base pad 61 adhered to the handle 11 at the base of the T-shaped slot 46 in which the carrier block 43 slides.

Right and left removable tooth supports 62, 63 are also provided for engaging one or more neighboring teeth on a distal side of the tooth to be extracted. The removable tooth supports 62, 63 each have a support arm 64, a support pad 65 attached at an end of the support arm 64, and pins 66 or other suitable structures for mounting the support arm 64 to receiving holes 67 provided in each respective side of the handle 11. The removable tooth supports 62, 63 provide a reaction force against the neighboring tooth or teeth on the distal side of the tooth to be extracted, similar to the reaction force provided by the base support 60 on the proximal side of the tooth to be extracted. As a result, the extraction force is evenly distributed on both sides of the tooth being extracted, and the extraction procedure is made highly controllable with minimum impact on the surrounding teeth.

The removable tooth supports 62, 63 are designed to have minimal height, to be removable, and to avoid interference with the tooth being pulled. The minimal height means that the patient's mouth does not have to be opened as wide. The tooth supports 62, 63 must be out of the way as to give the dentist plenty of room to manipulate the tool and see the extraction. This is enhanced by having right and left versions of the removable tooth supports 62, 63. A single support could be used if the support was symmetrical top and bottom, but such would not provide the benefits of a reduced profile in the limited space available within the patient's mouth. With right and left hand versions of the removable tooth supports 62, 63, the arm 64 of the support can be placed on the appropriate side for the most room to work around. By making the tooth supports 62, 63 removable, the tool can be more flexible in removing commonly pulled wisdom teeth, because these do not have space for a support beyond them.

When the base support 60 and one of the removable supports 62, 63 are in place, the load on each of the neighboring teeth is approximately half the force required to pull the tooth. This is considered a good well-distributed load. In addition, this loading does not require a reaction force on the handle 11 of the tool, thereby allowing the dentist more control in manipulating the tool because it is balanced.

In situations when the location of the tooth prevents using the removable support 62, 63, the base support 60 still provides a foundation to pull the tooth. The reaction force on the end of the handle 11 is on the order of 10% of the force to pull the tooth, depending on the exact length of the handle 11 and the distance from the clamp assembly 12, 39 to the base support 60.

The drive means in the preferred embodiments described above comprises a mechanical arrangement of components using a trigger 20 and a rack 24 and pinion 22 to pull a cable 15. The rack 24 and pinion 22 arrangement in the preferred embodiments has been oriented to create a logical and intuitive clamping action by squeezing the trigger 20 of the tool. The rack and pinion arrangement is also a simple, reliable, and cost-effective design.

Other simple gear trains with a rack and pinion or other gears could be rearranged for an easy-to-use method to pull the cable 15. A ratchet assembly could be added to the trigger to increase the leverage ratio. Mechanical solutions could also be implemented with work gears, or the trigger lever rotating a spool for the cable.

Hydraulic drive means could also be used for the tooth extraction device of this invention. Either a hydraulic motor that rotates a shaft to rotate the cable spool or a hydraulic cylinder could actuate the cable. The hydraulic cylinder could be either a single pull model or a double pull model depending on the connection to the cable. The key issue to a hydraulic unit would be creating a reliable unit that would be safe to use in or near a person's mouth.

An electric motor drive means could similarly actuate a cable spool or rack with a cable attached. This would have the advantage of fine on/off control without requiring the operator to apply force to the handle. Without having to squeeze the handle, the dentist could potentially be more precise in clamping and removing the tooth.

The tips of the clamp links 25, 26, 40, 41 in each of the embodiments described herein provide the critical point of contact with the tooth. The clamp links can be provided with a concave surface that wraps around the tooth, an edge to sever the ligaments at the base edge of the tip to make tooth extraction easier, a rubber pad to improve grip, and/or a textured surface to increase friction. The particular structure of the tips of the clamp links should be matched to the function that the tip performs, such as gripping different shaped teeth, cutting the ligaments that connect the tooth to the socket, and pulling caps. The present invention accommodates these different functions by allowing different specialized tips to be mounted on interchangeable carrier blocks 27, 43 with associated linkage. The user can thus remove the carrier block 27, 43 with its associated linkage and replace it with a different one with the appropriate tip for the desired function. Other possible ways of making the grips for the teeth modular to accommodate different functions include: providing removable insets that attach to the links to customize the gripping surface, or making the links 25, 26, 40, 41 modular so that the user would simply swap out the links to change the gripping surface.

In the preferred embodiments, the handle 11 has a smooth curving profile to comfortably fit in a dentist's hand to increase the level of control in manipulating the tool. Both the handle 11 and the trigger 20 have an oblong profile allowing the dentist to precisely position the tool. The rack 24 and pinion 22 are housed in a bulbous shape on the top of the handle 11. The larger handle section tapers to a small circle profile to house the cable 15. This provides the smallest tool inside the patient's mouth. The end of the handle 11 gradually curves down to provide a place for the clamp assembly 12, 39 to be attached.

The clamp assembly 12, 39 in each of the preferred embodiments attaches to the handle 11 via a T-slot 30, 46 to allow vertical motion, but not rotation in any direction. This is important in order to reduce the amount of force necessary to pull the tooth. The tooth has a root connected to the bone. The tooth is also connected to the periodontal socket in the gums via ligaments. The connection of the tooth to the bone can be weakened by rocking the tooth. This locally deforms the bone and allows the tooth to be pulled easier. The action is similar to rocking a tent stake in order to make it easier to remove. This movement reduces by an order of magnitude the force to pull the tooth. The T-slot 30, 46 in the handle 11 allows the dentist to rotate the tooth in any direction by creating a structure that transfers moments applied to the handle 11 to the tooth.

While the invention has been specifically described in connection with specific embodiments thereof, it is to be understood that this is by way of illustration and not of limitation, and the scope of the appended claims should be construed as broadly as the prior art will permit.

What is claimed is:

1. A tooth extraction device, comprising:
   a handle;
   a clamp assembly attached to said handle, said clamp assembly comprising a structure for clamping a tooth to be extracted; and
   a cable attached to the clamp assembly for moving the clamp assembly relative to the handle to extract a tooth;
   wherein said clamp assembly comprises a pair of clamp links pivotally connected to a carrier block, said clamp links being rotatable to engage opposite sides of a tooth, and said carrier block being movable relative to the handle to extract the tooth;
   wherein the carrier block is slidable relative to the handle; and
   wherein said clamp links and said carrier block are arranged such that movement of the cable in a first direction first causes said clamp links to rotate into engagement with opposite sides of a tooth and then subsequently causes said carrier block to slide along the handle to extract the tooth.

2. The tooth extraction device according to claim 1, wherein said structure for clamping a tooth comprises a pair of clamp links that engage opposite sides of the tooth.

3. The tooth extraction device according to claim 1, wherein said clamp assembly is attached to the handle such that moments applied to the handle are transferred to the tooth to be extracted.

4. The tooth extraction device according to claim 1, further comprising a manually operated trigger connected to the cable, said trigger being operable to move the cable relative to the handle.

5. The tooth extraction device according to claim 4, further comprising a pinion connected to the trigger for rotation with the trigger, and a rack connected to the cable, the rack and pinion being intermeshed such that rotation of the trigger causes movement of the cable and the clamp assembly relative to the handle.

6. The tooth extraction device according to claim 1, wherein said clamp assembly comprises a wedge attached to a free end of the cable, said wedge increasing in thickness in a direction away from the cable, and said clamp links each having a surface that engages a respective opposing side of said wedge, whereby movement of said wedge relative to said clamp links causes said clamp links to rotate on said carrier clamp assembly comprises a pair of toggle links connected to a free and of the cable, said toggle links each being connected to a respective one of said clamp links, whereby movement of said toggle links relative to said carrier block causes said clamp links to rotate on said carrier block.

7. The tooth extraction device according to claim 1, wherein said clamp assembly comprises a pair of toggle links connected to a free end of the cable, said toggle links each being connected to a respective one of said clamp links, whereby movement of said toggle links relative to said carrier block causes said clamp links to rotate on said carrier block.

8. The tooth extraction device according to claim 1, wherein said handle has a handgrip portion at a first end, the clamp assembly attached to a second end, and an elongated neck portion extending between the first and second ends, and wherein the cable extends through the neck portion to an actuator located within the handle.

9. The tooth extraction device according to claim 1, further comprising at least one support for engaging a neighboring tooth to provide a reaction force when extracting a tooth.

10. The tooth extraction device according to claim 9, wherein said at least one support comprises a base support for engaging a first neighboring tooth on a proximal side of the clamp assembly, and a removable tooth support for engaging a second neighboring tooth on a distal side of the clamp assembly.

11. A tooth extraction device, comprising:
    a handle;
    a clamp assembly attached to said handle, said clamp assembly comprising a pair of clamp links pivotally connected to a carrier block, said clamp links being rotatable to engage opposite sides of a tooth, and said carrier block being slidably movable relative to the handle to extract the tooth;
    a cable attached to the clamp assembly for moving the clamp assembly relative to the handle to extract a tooth;
    an actuator for moving the cable within the handle;
    a support for engaging a neighboring tooth to provide a reaction force when extracting a tooth; and
    wherein said clamp assembly and said carrier block are arranged such that movement of the cable in a first direction first causes said clamp links to rotate into engagement with opposite sides of a tooth and then subsequently causes said carrier block to slide along the handle to extract the tooth.

12. The tooth extraction device according to claim 11, further comprising a manually operated trigger connected to the cable, said trigger being operable to move the cable relative to the handle.

13. The tooth extraction device according to claim 12, further comprising a pinion connected to the trigger for rotation with the trigger, and a rack connected to the cable, the rack and pinion being intermeshed such that rotation of the trigger causes movement of the cable and the clamp assembly relative to the handle.

* * * * *